United States Patent
King et al.

(10) Patent No.: US 11,412,998 B2
(45) Date of Patent: Aug. 16, 2022

(54) MULTI-SOURCE MEDICAL DISPLAY

(71) Applicant: Karl Storz Imaging, Inc., Goleta, CA (US)

(72) Inventors: Timothy King, Goleta, CA (US); Thomas Prescher, Agoura Hills, CA (US); Kim Barnhill, Manhattan Beach, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 1413 days.

(21) Appl. No.: 14/048,913

(22) Filed: Oct. 8, 2013

(65) Prior Publication Data

US 2014/0037165 A1  Feb. 6, 2014

Related U.S. Application Data

(63) Continuation-in-part of application No. 13/289,554, filed on Nov. 4, 2011.
(Continued)

(51) Int. Cl.
*A61B 5/00* (2006.01)
*A61B 8/08* (2006.01)
(Continued)

(52) U.S. Cl.
CPC .............. *A61B 5/748* (2013.01); *A61B 6/032* (2013.01); *A61B 6/52* (2013.01); *A61B 8/52* (2013.01);
(Continued)

(58) Field of Classification Search
None
See application file for complete search history.

(56) References Cited

U.S. PATENT DOCUMENTS 4,216,589 A   8/1980  Beaver
4,559,705 A   12/1985 Hodge et al.
(Continued)

FOREIGN PATENT DOCUMENTS

EP   2486847 A1   8/2012
JP   H07184863 A  7/1995
WO   2010088515 A1 8/2010

OTHER PUBLICATIONS

European Search Report Application No. EP14166034 Completed: Aug. 25, 2014; dated Sep. 1, 2014 pp. 6.
(Continued)

*Primary Examiner* — Luther Behringer
(74) *Attorney, Agent, or Firm* — Whitmyer IP Group LLC

(57) ABSTRACT

A system for indicating an area of interest on an image, including a source of image data, an image processing unit, a user interface, and a destination, which may be a display. The image data may be ultrasound, X-ray, magnetic resonance imaging, nuclear magnetic resonance imaging, magnetic resonance tomography, computed tomography or surgical image data. The image processing unit may be configured to receive the image data from the source and combine it with a desired overlay pattern selected from a plurality of overlay patterns for indicating an area of interest on the image, which is then displayed on the display. The overlay pattern may include a key with coordinates or labels. Properties of the overlay pattern and the image data may be adjusted independently or automatically.

24 Claims, 18 Drawing Sheets

Related U.S. Application Data

(60) Provisional application No. 61/441,473, filed on Feb. 10, 2011.

(51) Int. Cl.
  *A61B 6/00* (2006.01)
  *G01R 33/54* (2006.01)
  *A61B 6/03* (2006.01)
  *G06T 7/00* (2017.01)
  *A61B 1/00* (2006.01)

(52) U.S. Cl.
  CPC ............ *G01R 33/54* (2013.01); *G06T 7/0012* (2013.01); *A61B 1/0005* (2013.01); *A61B 5/0077* (2013.01); *A61B 5/742* (2013.01)

(56) References Cited

U.S. PATENT DOCUMENTS

| | | | |
|---|---|---|---|
| 5,099,846 A * | 3/1992 | Hardy | A61N 5/1031 378/4 |
| 5,174,037 A | 12/1992 | Curtin | |
| 5,517,278 A | 5/1996 | Takahara et al. | |
| 5,573,492 A | 11/1996 | Dianna et al. | |
| 5,836,869 A | 11/1998 | Kudo et al. | |
| 6,037,936 A | 3/2000 | Ellenby et al. | |
| 6,359,644 B1 | 3/2002 | Salvati | |
| 6,414,696 B1 | 7/2002 | Ellenby et al. | |
| 6,431,768 B1 | 8/2002 | Nakamura | |
| 6,535,756 B1 | 3/2003 | Simon et al. | |
| 6,630,937 B2 | 10/2003 | Kallergi et al. | |
| 6,636,254 B1 * | 10/2003 | Onishi | A61B 1/0005 348/65 |
| 6,725,080 B2 | 4/2004 | Melkent et al. | |
| 7,033,172 B2 | 4/2006 | Hansen et al. | |
| 7,075,556 B1 | 7/2006 | Meier et al. | |
| 7,366,934 B1 | 4/2008 | Narayan et al. | |
| 7,427,263 B2 | 9/2008 | Hoeg et al. | |
| 7,492,363 B2 | 2/2009 | Meier et al. | |
| 7,590,335 B2 | 9/2009 | Kobayashi et al. | |
| 7,607,079 B2 | 10/2009 | Reiner | |
| 7,782,384 B2 | 8/2010 | Kelly | |
| 7,811,224 B2 | 10/2010 | Hale et al. | |
| 7,849,024 B2 | 12/2010 | Lee et al. | |
| 7,864,996 B2 | 1/2011 | Hemmer et al. | |
| 7,907,166 B2 | 3/2011 | Lamprecht et al. | |
| 7,949,965 B2 | 5/2011 | Tominaga | |
| 8,073,528 B2 | 12/2011 | Zhao et al. | |
| 8,213,788 B2 | 7/2012 | Soll et al. | |
| 8,600,133 B2 | 12/2013 | Buelow et al. | |
| 8,830,224 B2 | 9/2014 | Zhao et al. | |
| 2002/0026093 A1 * | 2/2002 | Ooyatsu | A61B 1/00188 600/118 |
| 2002/0049375 A1 | 4/2002 | Strommer et al. | |
| 2003/0069975 A1 | 4/2003 | Abjanic et al. | |
| 2003/0083563 A1 * | 5/2003 | Katsman | G01S 7/52084 600/407 |
| 2003/0114730 A1 | 6/2003 | Hale et al. | |
| 2004/0085455 A1 | 5/2004 | Silverstein | |
| 2004/0127769 A1 * | 7/2004 | Hale | A61B 1/00039 600/173 |
| 2005/0065435 A1 * | 3/2005 | Rauch | A61B 34/73 600/427 |
| 2005/0075535 A1 | 4/2005 | Shapiro et al. | |
| 2005/0085717 A1 * | 4/2005 | Shahidi | A61B 8/0841 600/424 |
| 2005/0093889 A1 * | 5/2005 | Sauer | G06T 19/003 345/633 |
| 2005/0146622 A9 | 7/2005 | Silverstein | |
| 2005/0177026 A1 | 8/2005 | Hoeg et al. | |
| 2005/0187432 A1 * | 8/2005 | Hale | A61B 1/00009 600/118 |
| 2006/0098112 A1 | 5/2006 | Kelly | |
| 2006/0142657 A1 * | 6/2006 | Quaid | A61N 1/372 600/424 |
| 2006/0152516 A1 | 7/2006 | Plummer | |
| 2006/0217689 A1 | 9/2006 | Dick et al. | |
| 2006/0257008 A1 | 11/2006 | Nolle et al. | |
| 2006/0258938 A1 | 11/2006 | Hoffman et al. | |
| 2006/0259193 A1 | 11/2006 | Wang et al. | |
| 2007/0073161 A1 | 3/2007 | Davidson | |
| 2007/0106282 A1 | 5/2007 | Lavallee | |
| 2007/0147707 A1 | 6/2007 | Coste-Maniere et al. | |
| 2007/0156017 A1 * | 7/2007 | Lamprecht | A61B 1/00193 600/102 |
| 2007/0269092 A1 | 11/2007 | Hill et al. | |
| 2008/0004603 A1 | 1/2008 | Larkin et al. | |
| 2008/0015415 A1 | 1/2008 | Obata et al. | |
| 2008/0071142 A1 | 3/2008 | Gattani et al. | |
| 2008/0192116 A1 | 8/2008 | Tamir et al. | |
| 2008/0303899 A1 | 12/2008 | Berci | |
| 2009/0036902 A1 | 2/2009 | DiMaio et al. | |
| 2009/0087067 A1 | 4/2009 | Khorasani | |
| 2009/0088634 A1 | 4/2009 | Zhao et al. | |
| 2009/0088897 A1 | 4/2009 | Zhao et al. | |
| 2009/0146950 A1 | 6/2009 | Maringelli | |
| 2009/0156895 A1 | 6/2009 | Higgins et al. | |
| 2009/0171184 A1 | 7/2009 | Jenkins et al. | |
| 2009/0190808 A1 | 7/2009 | Claus | |
| 2009/0235570 A1 | 9/2009 | Sammut et al. | |
| 2009/0271738 A1 | 10/2009 | Glaser-Seidnitzer et al. | |
| 2009/0276725 A1 | 11/2009 | Glaser-Seidnitzer et al. | |
| 2010/0094085 A1 | 4/2010 | Yamamoto et al. | |
| 2010/0160789 A1 | 6/2010 | Dilworth et al. | |
| 2010/0166323 A1 | 7/2010 | Zhao et al. | |
| 2010/0168765 A1 | 7/2010 | Moraviec | |
| 2010/0228249 A1 | 9/2010 | Mohr et al. | |
| 2011/0135149 A1 | 6/2011 | Gefen | |
| 2011/0137156 A1 | 6/2011 | Razzaque et al. | |
| 2011/0141140 A1 * | 6/2011 | Duhamel | G06T 7/0012 345/629 |
| 2011/0170755 A1 | 7/2011 | Buelow et al. | |
| 2011/0235891 A1 | 9/2011 | Sonnemans et al. | |
| 2012/0038744 A1 | 2/2012 | Naka | |
| 2012/0158019 A1 | 6/2012 | Tenney et al. | |
| 2012/0209123 A1 | 8/2012 | King | |
| 2013/0197357 A1 | 8/2013 | Green et al. | |
| 2014/0037165 A1 | 2/2014 | King et al. | |
| 2014/0051986 A1 | 2/2014 | Zhao et al. | |
| 2014/0055489 A1 | 2/2014 | Itkowitz et al. | |
| 2014/0111623 A1 | 4/2014 | Zhao et al. | |
| 2014/0142422 A1 | 5/2014 | Manzke et al. | |
| 2014/0176661 A1 | 6/2014 | Smurro et al. | |
| 2014/0267603 A1 | 9/2014 | Kerdok et al. | |
| 2014/0275760 A1 | 9/2014 | Lee et al. | |

OTHER PUBLICATIONS

Yang et al., "Informatics in Radiology (infoRAD) Multimedia Extension of Medical Imaging Resource Center Teaching Files", RadioGraphics 2005; 25:1699-1708.

Adler et al., "Overlay of Patient-Specific Anatomical Data for Advanced Navigation in Surgery Simulation", IWDE 2010 Magdeburg, Germany.

European Office Action Application No. 14188189.6 Completed: Dec. 17, 2015 4 Pages.

Canadian Office Action Application No. 2,766,595 dated May 3, 2015 Completed: Apr. 27, 2016 5 Pages.

European Office Action Application No. 12154966.1 dated Mar. 22, 2016 4 Pages.

European Search Report Application No. EP 12 15 4966 Completed: May 31, 2012; dated Jun. 12, 2012 6 pages.

European Search Report Application No. EP 14 18 8189 Completed: Mar. 19, 2015; dated Mar. 27, 2015 6 pages.

European Office Action Application No. 12154966.1 Completed Date: Nov. 7, 2017 4 Pages.

U.S. Office Action U.S. Appl. No. 13/871,672 dated Apr. 11, 2016 16 Pages.

U.S. Office Action U.S. Appl. No. 13/871,672 dated Apr. 12, 2017 13 pages.

U.S. Office Action U.S. Appl. No. 13/871,672 dated Jul. 28, 2016 14 Pages.

(56) References Cited

OTHER PUBLICATIONS

U.S. Office Action U.S. Appl. No. 13/871,672 dated Aug. 24, 2017 13 pages.
U.S. Office Action U.S. Appl. No. 14/048,913 dated Sep. 19, 2017 22 pages.
U.S. Office Action U.S. Appl. No. 13/871,672 dated Dec. 1, 2016 15 Pages.
European Office Action Application No. 14166034.0 Completed: Jul. 5, 2018 4 Pages.
U.S. Office Action U.S. Appl. No. 13/289,554 dated Apr. 29, 2019 21 Pages.

* cited by examiner

MULTI-SOURCE MEDICAL DISPLAY

FIELD OF THE INVENTION

The present invention relates to a system for displaying medical images. Specifically, the present invention relates to a method and apparatus for generating an overlay aid on medical images.

BACKGROUND OF THE INVENTION

In modern medicine, treatments are being carried out more and more using technical imaging methods. By way of example, miniaturized cameras are inserted into the body of a patient, and the image taken by the camera is displayed to the physician on a monitor installed in his/her working area. In this way, the physician can, for example, examine an internal organ or a joint for diagnostic purposes and he/she can also carry out surgical operations in a minimally invasive fashion. By arranging a monitor in the working area of the physician, i.e. in the sterile area, the physician may track all the operations that he or she undertakes on the patient live on the monitor, the corresponding monitor image being picked up by the medical imaging system. Accordingly, during various types of minimally invasive surgeries, such as, endoscopic, arthroscopic and laparoscopic procedures, a surgeon is able to visibly examine the interior of an organ, joint or other anatomical structure while the surgeon is conducting the surgery.

Recent developments have resulted in systems incorporating various audiovisual devices to allow others in the surgical suite or located remotely therefrom who may be assisting or observing, to better monitor the surgical procedure. Accordingly, both still images and live video being acquired during the surgery, can be output to various different monitors or recording devices both within, and outside of the surgical suite. Additionally, various devices have been incorporated into these systems to allow the surgeon, or other individuals assisting or observing, to utilize the imaging capabilities of the system in different ways, simultaneously or at different times, for a variety of different objectives.

Moreover, when there are multiple persons assisting in or observing a surgery, it is often necessary to call attention to or identify certain areas of interest within the patient's body shown on a live surgical monitor. For example, an instructor may wish to call attention to certain internal organs or structures, pathologies or procedures to students while observing a surgery. In addition, a supervising surgeon may direct the main practitioner to add more sutures in an area of interest.

In order to further improve communication during these surgical procedures, it is desired to have a method or device for calling attention to or identifying certain areas of interest displayed on the live surgical monitor. This would facilitate efficient and clear communication regarding a particular area of interest and diminish confusion, misunderstandings and misinterpretations.

Certain methods and devices have been tried to identify regions of interest on a live surgical monitor, including, use of a laser pointer or cursor or "circling" or annotating on a touch screen by the surgeon or assistants, or others assisting in or observing the surgery. These known methods have many disadvantages. First, the surgeon cannot operate a laser pointer or make indications on a touch screen while also safely performing the surgical procedure. Second, these known methods, including the use of a cursor, require the use of an additional hand, which the surgeon often cannot spare.

SUMMARY OF THE INVENTION

Against this background, it is an object of the present invention to provide a method and an apparatus for indicating regions of interest on images displayed on a monitor.

It is another object of the invention to provide such a method and apparatus in a simple and cost effective way.

It is another object of the invention that the image properties of the method and/or apparatus for indicating regions of interest be configurable and adjustable.

It is yet another object of the invention to enable a physician to configure and adjust the properties of the image in and around an identified region of interest.

In accordance with one aspect of the invention, a configurable overlay pattern for indicating regions of interest on a medical or surgical image is provided. The areas of interest defined by the overlay pattern may be labelled with coordinates, such as numbers and/or letters, for ease of reference. If, for example, the overlay pattern is a grid, the rows and columns of the grid may be labelled with Cartesian coordinates. In accordance with another aspect of the invention, the properties of the image in and/or around an identified region of interest may be adjusted. The overlay pattern may be applied to displayed images recalled from an image archive. The applied overlay pattern may also be maintained on captured images that are subsequently saved to an archive.

The novel method and apparatus have the advantage that the image including the overlay pattern is directly available for further processing outside the sterile area. This further processing can include, for example, displaying on a remote training monitor and/or archiving in an electronic patient card file. The novel system therefore offers an extended field of application.

In accordance with another aspect of the invention, a system for indicating an area of interest on a surgical image, comprising a camera for generating surgical image data; a camera control unit receiving processing said surgical image data from said camera; software executing on said camera control unit for applying an overlay pattern to said surgical image data; and a display controlled by said camera control unit for displaying said surgical image data and said overlay pattern, is provided. The system may also include a storage device for saving the surgical image data and the overlay pattern. The surgical image data may be video data, still frame data or combinations thereof. The overlay pattern itself may comprise a grid, crosshairs, quadrants, one or more hash marks, a circle or an oval and the pattern may be applied centered on the image as displayed or at the edges. A key for indicating one or more regions of the overlay pattern may also be provided. At least one property of the overlay pattern may also be adjustable, including brightness, contrast, opacity, resolution and color. The properties of the overlay may be adjusted via one or more buttons located on said camera, via a touch screen or via voice recognition software executing on the camera control unit.

In accordance with a further aspect of the invention, a system for indicating an area of interest on an image, comprising a source of image data; an image processing unit in communication with said source, the image processing unit being configured to receive the image data and combine it with an overlay pattern for indicating an area of interest; and a destination (e.g., a monitor) in communication with said image processing unit for receiving said image data combined with said overlay pattern, is provided. The system may also include a plurality of overlay patterns and a user interface for receiving the plurality of overlay patterns and selecting at least one overlay pattern from the plurality of overlay patterns. The system may further include software executing on said image processing unit for combining the image data with the selected overlay pattern. The source of image data, which may be video data, still frame data and combinations thereof, may be a camera, a storage medium, or a camera control unit. The destination may be a display, which may be configured to simultaneously display image data from more than one source in combination with an overlay pattern, or a storage medium.

The source of image data, the image processing unit for receiving the image data and combining it with an overlay pattern, and the monitor for displaying the overlayed image data of the above system may be located at different places, remotely from each other. For instance, a source of image data may be generated by a surgeon in an operating room; the image data may be processed and combined with an overlay pattern outside the operating room (for example in a pathology laboratory); and then the overlayed image data may be output to various different monitors both within, and outside of the operation room for being observed by the surgeon and/or other individuals assisting or observing, simultaneously or at different times, for a variety of different objectives.

In accordance with yet another aspect of the invention, a method for indicating an area of interest on an image, comprises the steps of providing a source of image data; transmitting the image data to an image processing unit from the source; combining the image data with an overlay pattern in the image processing unit to generate overlayed image data; transmitting the overlayed image data to a display; and displaying said image data combined with said overlay pattern on said display, is provided. Software executing on the image processing unit for combining the image data with the overlay pattern may also be provided. The method may also include the step of saving the overlayed image data to a storage medium in communication with the image processing unit. The method may further comprise the steps of providing a plurality of overlay patterns and selecting a desired pattern, adjusting the source of image data such that an area of interest is located near a region of said overlay pattern, and indicating an area of interest in said image data by referencing said overlay pattern.

In addition to the above mentioned overlay patterns, the overlay patterns for the display may comprise centric lines, concentric shapes, or a combination thereof. Preferably, the concentric shapes are concentric ovals, concentric circles, and concentric polygons. In some embodiments, the diameters of the concentric circles are at 25% and 50% of the height of said display. In other embodiments, the centric lines originate from a single point and are shown for every 15 degrees, 20 degrees, 30 degrees, 45 degrees, 60 degrees, or 90 degrees.

The system in accordance with the present invention may comprise multiple sources of image data, which include, but are not limited to, sources of ultrasound, X-ray, Magnetic resonance imaging (MRI), nuclear magnetic resonance imaging (NMRI), magnetic resonance tomography (MRT), computed tomography (CT), and surgical image data. The sources of image data may come from an archived image file. The image data may be video data, still frame data or combinations thereof, which can be streaming in from a hospital system.

It goes without saying that the features mentioned above and those yet to be explained below can be used not only in the combination respectively specified, but also in other combinations or on their own without departing from the scope of the present invention.

DETAILED DESCRIPTION OF THE INVENTION

The present invention provides a system 10 for indicating certain areas of interest in medical or surgical image data by applying an overlay pattern, such as a Cartesian grid, crosshairs, quadrants, etc., on the image. The overlay pattern allows a doctor to then refer or call attention to areas of interest in the image data by referencing the overlay pattern or a portion thereof. As will be discussed in detail below, the overlay may also include an key, which may include alphanumeric labels or coordinates, which may assist the doctor in indicating the area or portion of the overlay to which he/she is referring.

Figure 1:
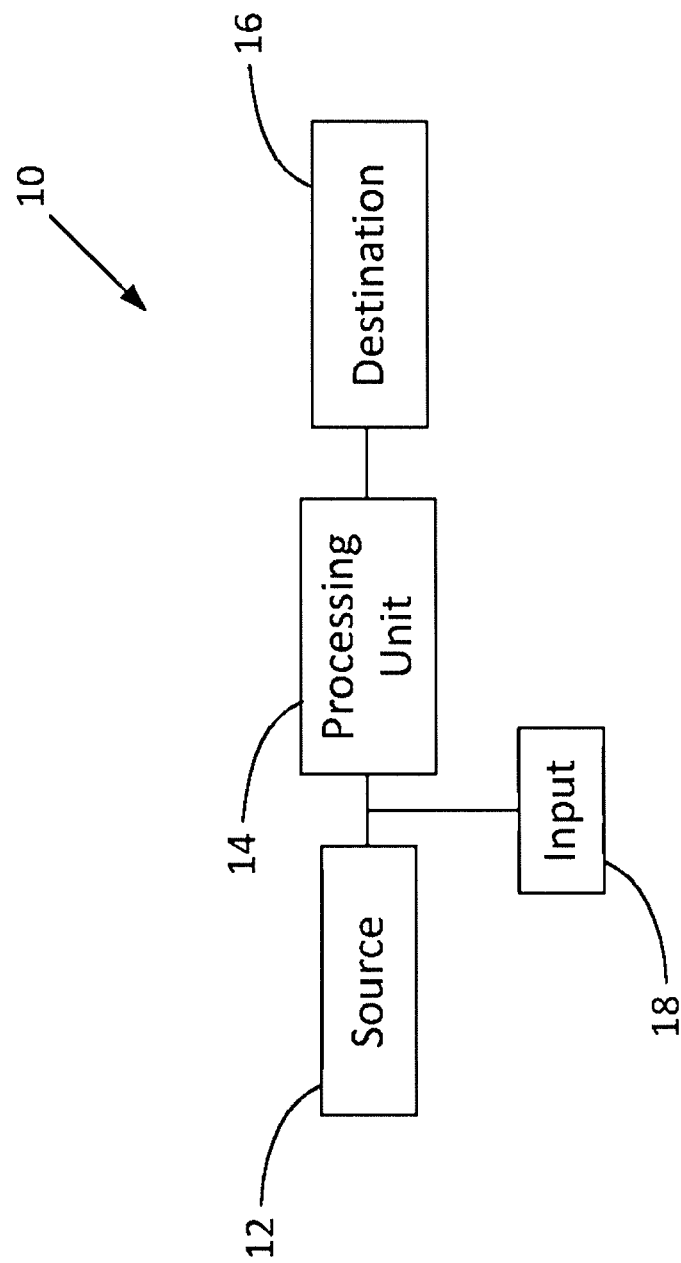
FIG. 1 is a schematic illustration of one embodiment of a system for indicating an area of interest on an image.

Referring to FIG. 1, the system 10 includes at least one source 12 of image data in communication with at least one processing unit 14 and at least one destination 16 for the image data. The at least one source 12 of image data connected to the processing unit 14 may include any device, system, or network that generates, acquires, stores, monitors, modifies, or controls image data for use in generating medical images, such as still frame images or video. For example, the at least one source 12 may include an image acquisition device, such as endoscopic cameras, video endoscopes, room cameras, light cameras, and boom cameras. Likewise, the at least one source 12 may include any recording, storage, and/or archival device or system, such as traditional video cassette recorders or digital video recording devices (such as a linear tape deck, DVD (Digital Versatile Disc), or DVR (digital video recorder), image capture devices, a PACS (Picture Archiving and Communication System) computer, or an HIS (Hospital Information System). Finally, the at least one source 12 may include any other device from which image data may be received, such as a patient monitor or a central computer for controlling various devices, or may simply be auxiliary inputs for connecting external devices that may supply image data to the system.

Additionally, a source 12 may be a source of medical or surgical image data that receives the image data from yet another source. For example, a source may be a linear tape deck that is recording live video as it supplies the video to the computer. The linear tape deck, in turn, may receive the live video from an endoscopic camera presently being used on a patient, as is further described below. As another example, a source 12 may be a processor for routing images from multiple other sources to the processing unit (i.e., a screen splitter), such as a quad image processor. The source 12 connected to the processing unit may also be a CCU (camera control unit).

The at least one processing unit 14 may include any device, system, or network that can process images generated from image data. For example, the processing unit 14 may be a general processor, a computer, or a CCU, which may be integrated in a camera or may be a modular CCU external to the camera.

The at least one destination 16 for the image data supplied by the at least one source 12 may include any device, system, or network that displays images generated from the image data, or otherwise communicates the image data to viewers, or stores the image data. For example, the at least one destination may include any of various displays, such as, for example, a flat panel display, a plasma screen, or a computer monitor. Additionally, the at least one destination may include a recording device or a storage medium.

Further, the at least one destination 16 for the surgical image data may be located within the operating room, or it may be at a location remote from the operating room. One object of the invention is to assist all those viewing or analyzing surgical image data to identify areas of interest in the surgical image data. For example, an overlay pattern applied to surgical image data may be used by a surgeon performing the surgery to communicate with an assisting surgeon that is not present in the operating room, but who is able to view the surgical image data with the overlay pattern on a destination 16, such as a monitor, at some other remote location. Further, the overlay pattern may be applied to surgical image data displayed on a monitor located in a lecture hall or classroom for teaching purposes.

Moreover, the destination 16 may be capable of displaying image data from more than one source. For example, the destination 16 may be a monitor with picture-in-picture (PIP) capabilities. In this embodiment, the user may choose to apply (or presets may set) an overlay pattern to all or some sets of image data displayed on the monitor. Similarly, if there are several destinations 16 for image data from several sources 12, then user may choose to apply (or presets may set) an overlay pattern to all or some sets of image data sent to the destinations 16.

As illustrated in FIG. 1, the system 10 may also include at least one input 18 in communication with the at least on source 12 and/or the processing unit 14. The at least one input 18 may include any interface whereby a user to enable/disable and/or adjust the properties of the overlay pattern. In one embodiment, the input 18 may be a button or menu located on the source 12, such as an endoscopic camera, itself. Alternatively, the input 18 may be a user interface that may include physical buttons for a doctor to press, or may also include a touch-screen monitor.

Figure 2:
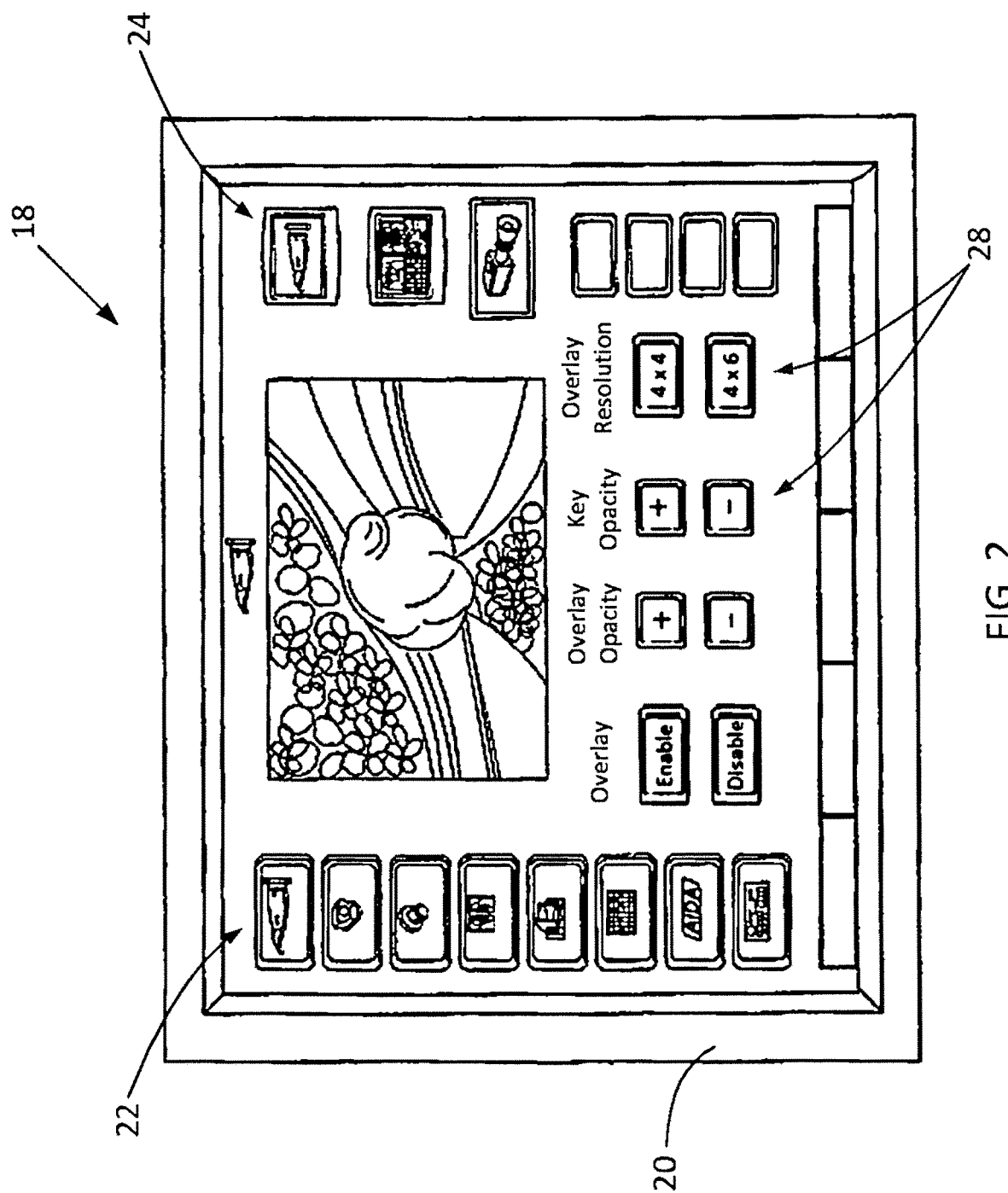
FIG. 2 is a view of an embodiment of an input for use with the system for indicating an area of interest on an image as shown in FIG. 1, 1a, or 1b.

In another embodiment, shown in FIG. 2, the input 18 may include one or more icons on a touch screen 20. In this embodiment, the system 10 may include software executing on the processing unit 14 that causes the touch screen 20 to simultaneously display several icons. The icons are sensitive to the touch of the user and will cause a command to be sent to the processing unit 14. By pressing certain source icons 22 or destination icons 24, the user can select a particular source and destination by pressing the touch screen 20 at the locations of the icon. The user can also manipulate or alter the images being displayed in the display window 26 on the touch screen in order to affect the images ultimately being communicated to the destinations. For example, the touch screen 20 may also include at least one icon 28 which allows the user to enable/disable the overlay pattern, adjust the properties of the overlay pattern, and select which image data to which the overlay pattern will be applied and to which destination 16 the combined image will be transmitted.

In some embodiments, the system 10 may also be configured to accept voice commands, allowing the user to vocally enable or disable the overlay pattern and adjust properties of the overlay pattern itself without having to touch the imaging device or user interface. In this embodiment, the at least one input 18 may include voice recognition software executing on said processing unit 14 for accepting voice commands, allowing the doctor to vocally enable or disable the overlay and adjust properties of the overlay itself without having to physically touch the source 12, processing unit 14 or input 18 themselves.

In some further embodiments, the input 18 may include accelerometer data (not shown) from the camera head or image motion vector detection. The overlay pattern may be automatically enabled or disabled or the properties of the overlay pattern may be adjusted in response to the input of this data.

The input 18 may also include preset data saved by the user that will act on the processing unit 14 to enable/disable the overlay pattern at certain times as preset by the user. The preset data may also include the preferred type of overlay pattern and/or the properties of the overlay pattern the user desires to be sent to the destination 16.

Figure 5:
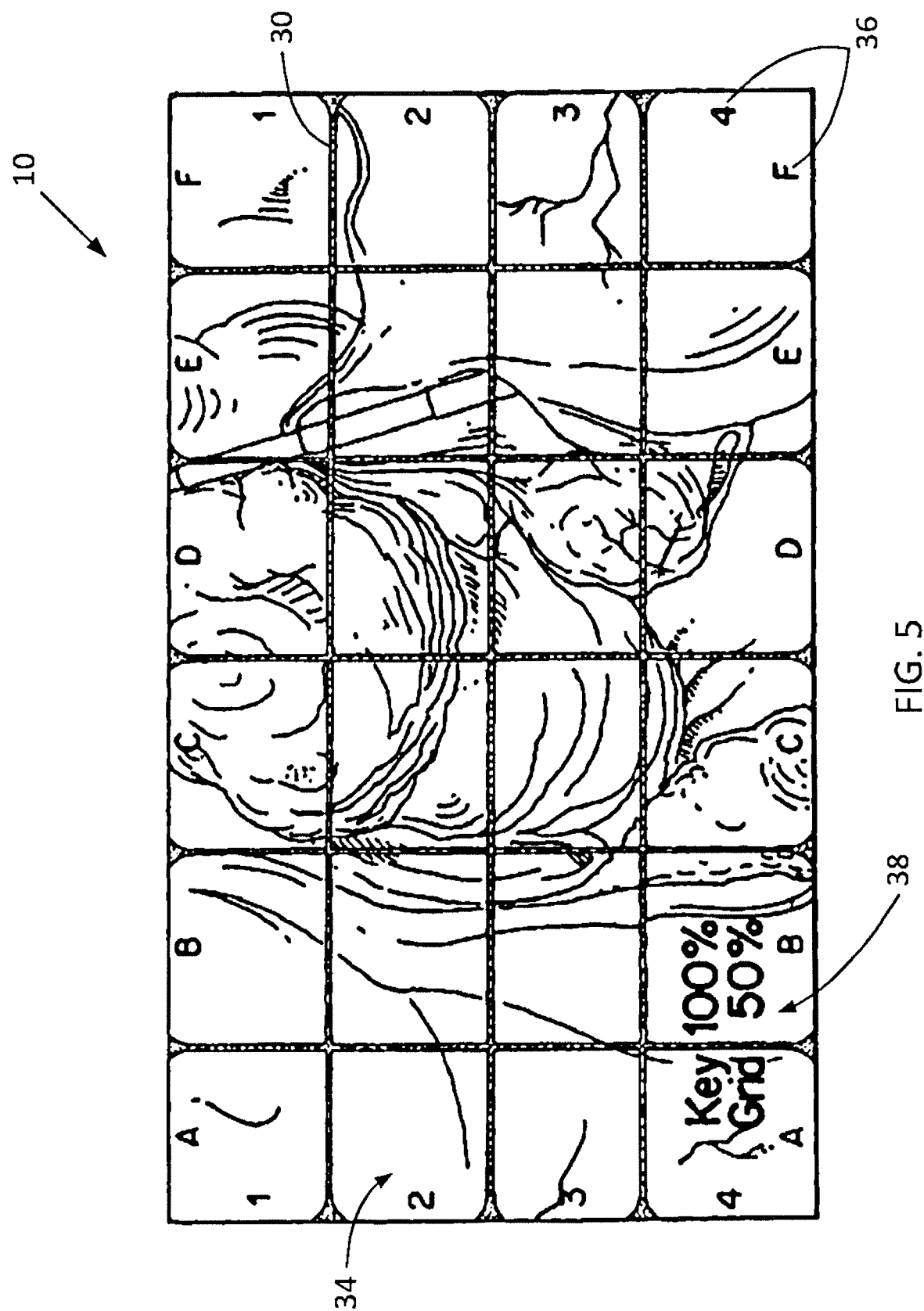
FIG. 5 is a view of an overlay pattern combined in the form of a grid at 50% opacity and a key at 100% opacity, combined with image data, for use with the system for indicating an area of interest on an image as shown in FIG. 1, 1a, or 1b.
Figure 6:
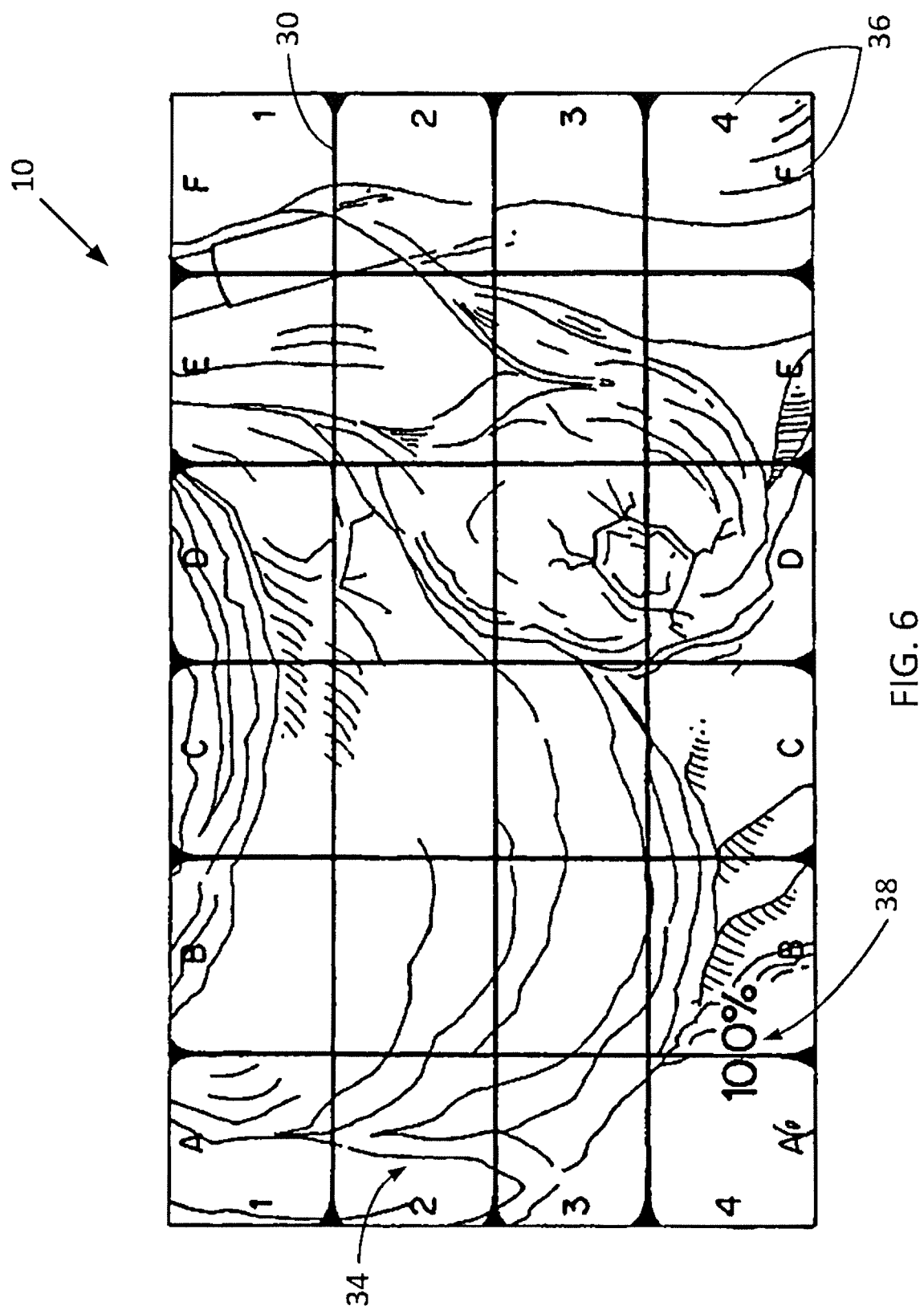
FIG. 6 is a view of an overlay pattern in the form of a grid with a key, both at 100% opacity, combined with image data, for use with the system for indicating an area of interest on an image as shown in FIG. 1, 1a, or 1b.
Figure 7:
FIG. 7 is a view of an overlay pattern in the form of a centered crosshairs, combined with image data, for use with the system for indicating an area of interest on an image as shown in FIG. 1, 1a, or 1b.
Figure 8:
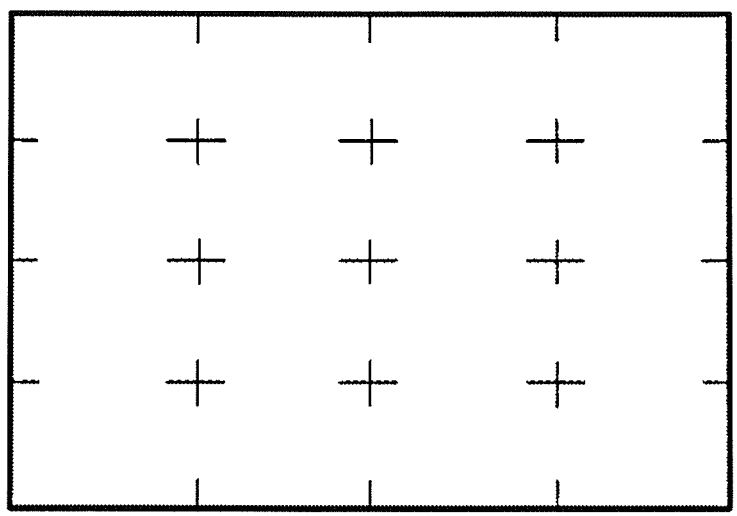
FIG. 8 is a view of an overlay pattern for use with the system for indicating an area of interest on an image as shown in FIG. 1, 1a, or 1b.
Figure 9:
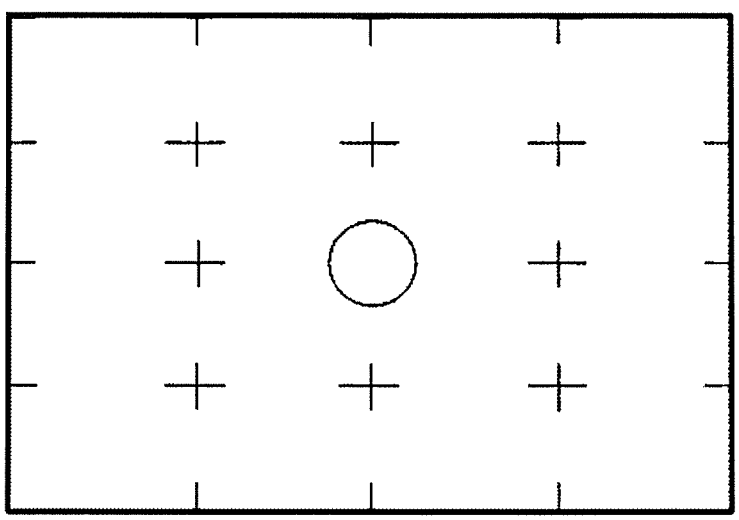
FIG. 9 is a view of an overlay pattern for use with the system for indicating an area of interest on an image as shown in FIG. 1, 1a, or 1b.
Figure 10:
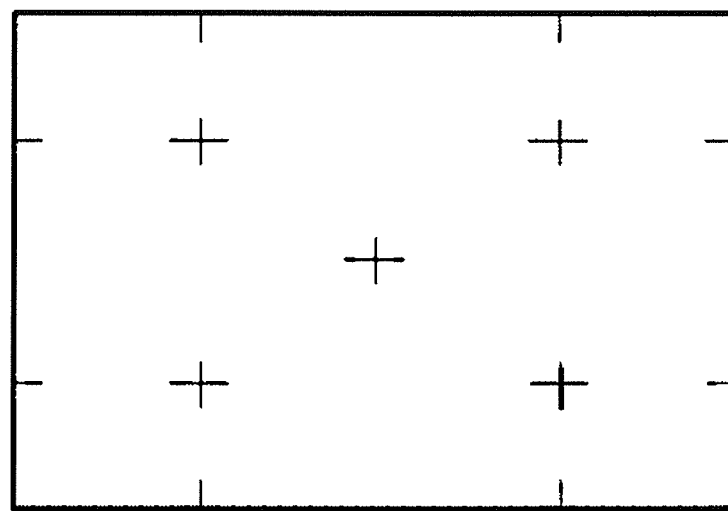
FIG. 10 is a view of an overlay pattern for use with the system for indicating an area of interest on an image as shown in FIG. 1, 1a, or 1b.

As shown in FIGS. 3 and 7-21, the overlay pattern 30 may be provided in any number of designs, which may be set by the user. For example, as shown in FIGS. 3-6, the overlay pattern 30 may be a grid. In addition, as shown in FIG. 7, the overlay pattern 30 may include a single crosshairs placed at the center of the image as displayed. In other embodiments, the overlay pattern may be one or more hash marks or crosshairs overlaid across a portion of the image, the entire image, or at the edges of the image. The overlay may also be separated into quadrants, with any number of circles, ovals hash marks or any combination thereof within the quadrants. The overlay may also be one or more circles, ovals or other shapes.

The desired overlay pattern 30 may be chosen by the user through an input 18, some examples of which are described above. For example, the source 12, such as an endoscopic camera, may include buttons for selecting and setting a desired overlay pattern 30. The user may also chose to apply the overlay pattern 30 to one, some, or all of the sources 12 of image data 34. Once the overlay pattern 30 is selected, the image data 34 from the one or more selected sources 12 may be combined with the overlay pattern 30 in the processing unit 14 and the combined image transmitted to the one or more selected destinations 18.

Figure 3:
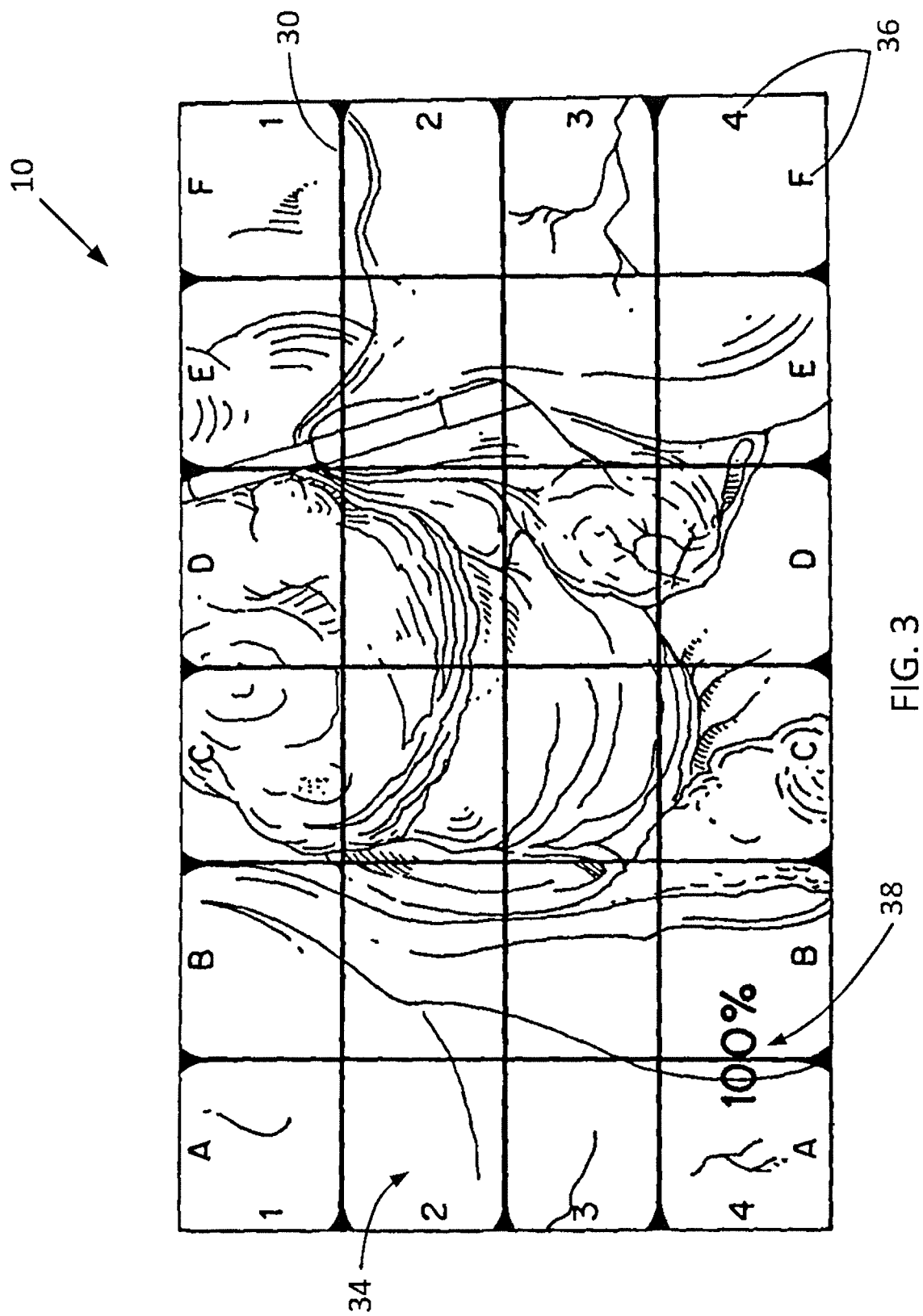
FIG. 3 is a view of an overlay pattern in the form of a grid with a key, both at 100% opacity, combined with image data, for use with the system for indicating an area of interest on an image as shown in FIG. 1, 1a, or 1b.

In one embodiment, the overlay pattern may be applied to live images, in real time. For example, as shown in FIG. 3, the combined image data 34 and overlay pattern 30 may be transmitted to a display 32. The display may be located in the operating room and/or it may be located somewhere remote from the operating room for viewing by other surgeons assisting in the surgery or by students observing the surgery for educational purposes.

Further, the overlay pattern 30 may be applied to image data 34 that has been recalled from an image archive, such as on a storage medium. The applied overlay pattern 30 may also be maintained on captured image data 34 that is subsequently saved to an archive and may be recalled later for viewing on a display.

The overlay pattern 30 may be applied to the image data at a "fixed" position, meaning that the overlay 30 will be applied at a fixed position with respect to the displayed image, i.e., centered on the image. However, the user may adjust the image data 34 separately with respect to the overlay pattern 30. In operation, the user views the image data with the overlay pattern 30 on a display 32 and adjusts the image captured by the source 12 (i.e., a camera) until the particular area of interest is located at or near an identifiable region of the overlay pattern 30. Using the embodiment shown in FIG. 7, the doctor will adjust the field of view of the camera until the area of interest is centered at the crosshairs. This enables the doctor to unequivocally "point" to the area of interest, simply by adjusting the camera.

Figure 11:
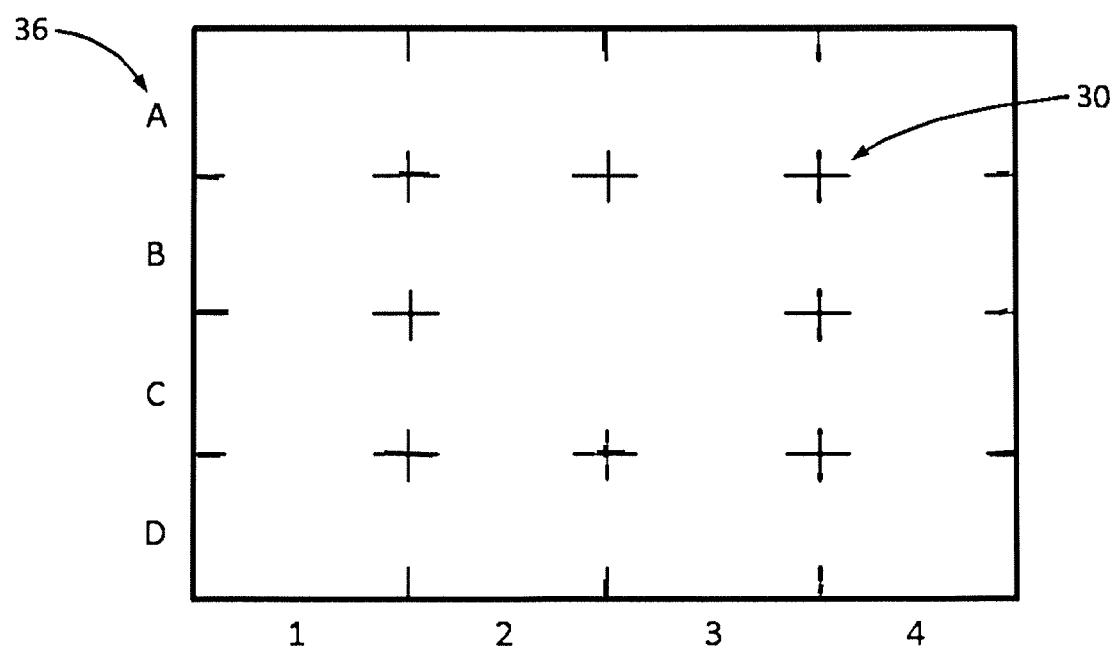
FIG. 11 is a view of an overlay pattern for use with the system for indicating an area of interest on an image as shown in FIG. 1, 1a, or 1b.
Figure 12:
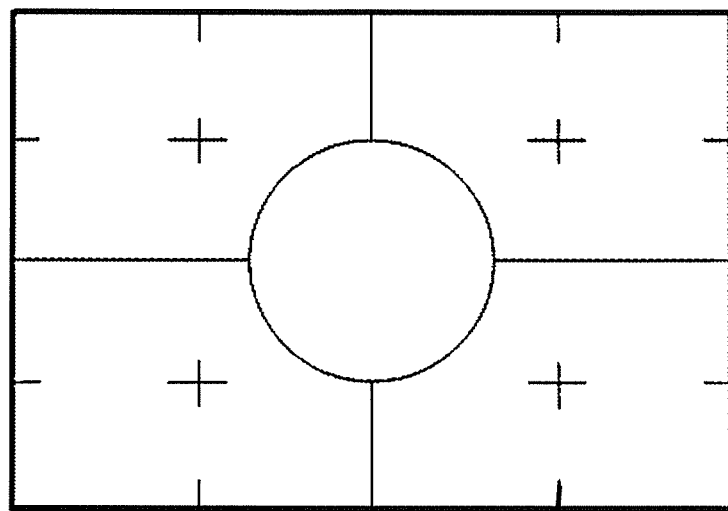
FIG. 12 is a view of an overlay pattern for use with the system for indicating an area of interest on an image as shown in FIG. 1, 1a, or 1b.
Figure 13:
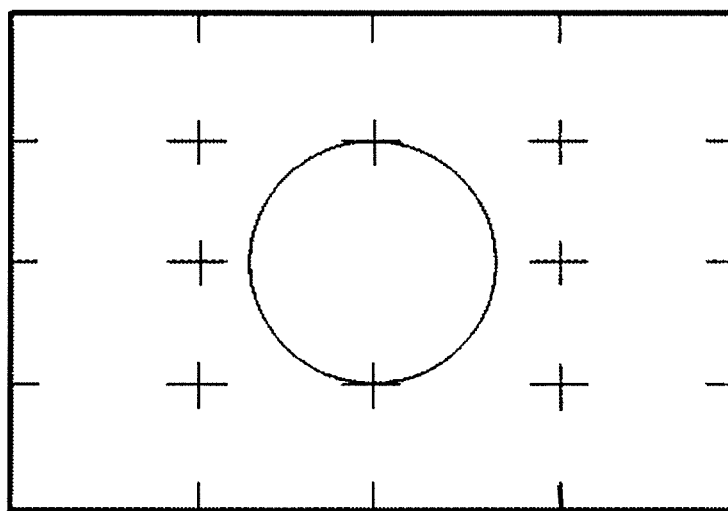
FIG. 13 is a view of an overlay pattern for use with the system for indicating an area of interest on an image as shown in FIG. 1, 1a, or 1b.
Figure 16:
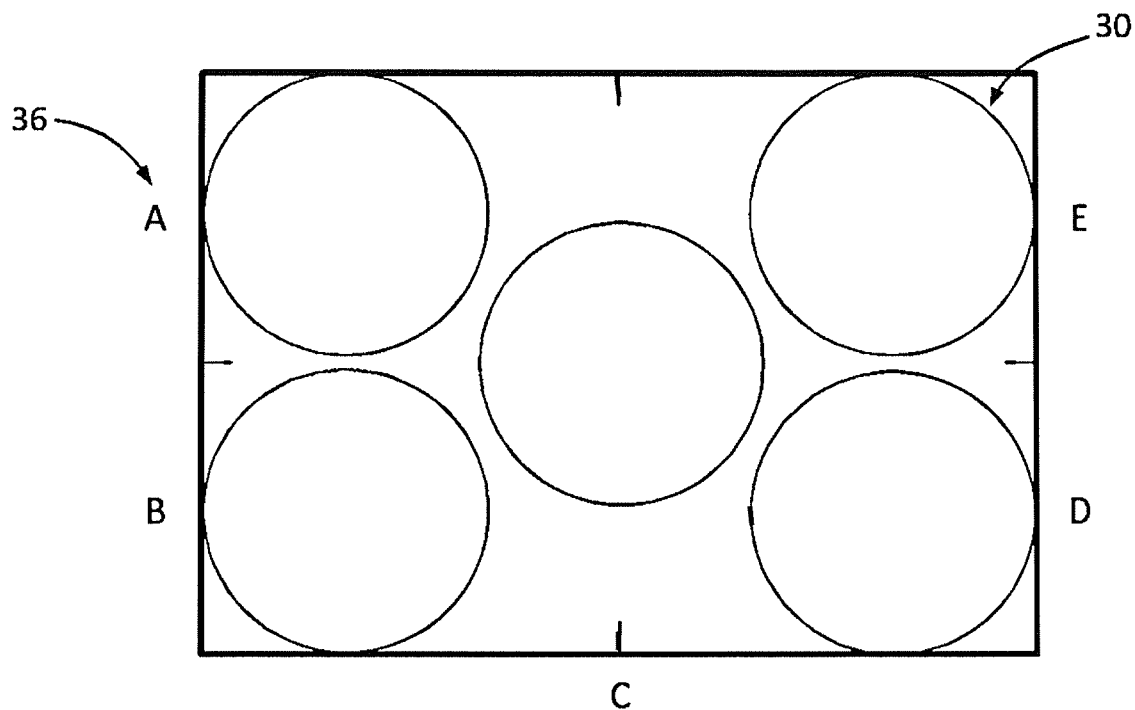
FIG. 16 is a view of an overlay pattern for use with the system for indicating an area of interest on an image as shown in FIG. 1, 1a, or 1b.
Figure 17:
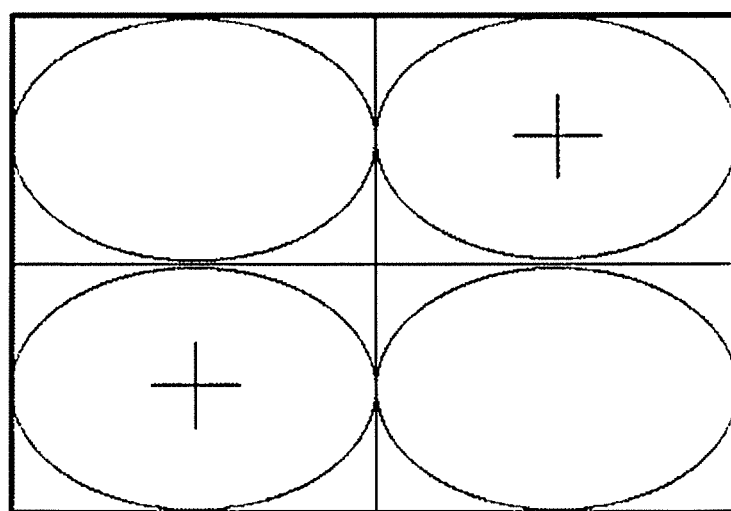
FIG. 17 is a view of an overlay pattern for use with the system for indicating an area of interest on an image as shown in FIG. 1, 1a, or 1b.
Figure 18:
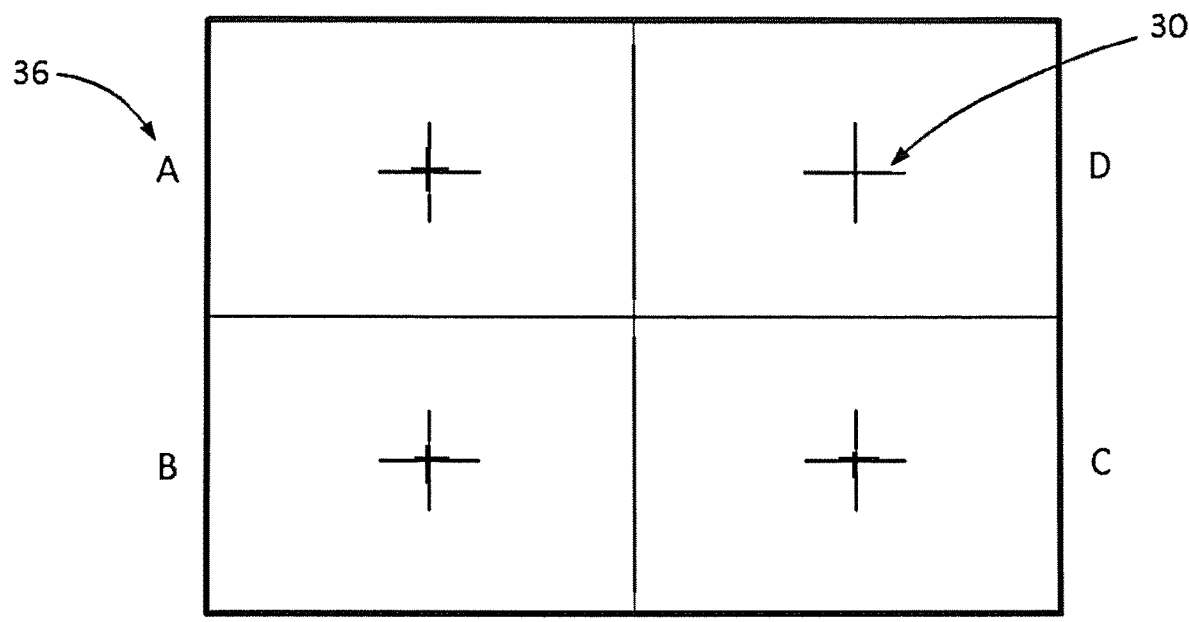
FIG. 18 is a view of an overlay pattern for use with the system for indicating an area of interest on an image as shown in FIG. 1, 1a, or 1b.
Figure 19:
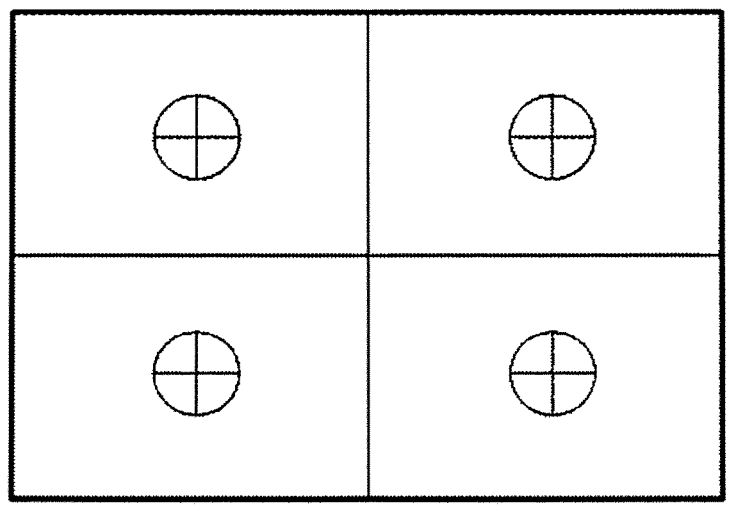
FIG. 19 is a view of an overlay pattern for use with the system for indicating an area of interest on an image as shown in FIG. 1, 1a, or 1b.
Figure 20:
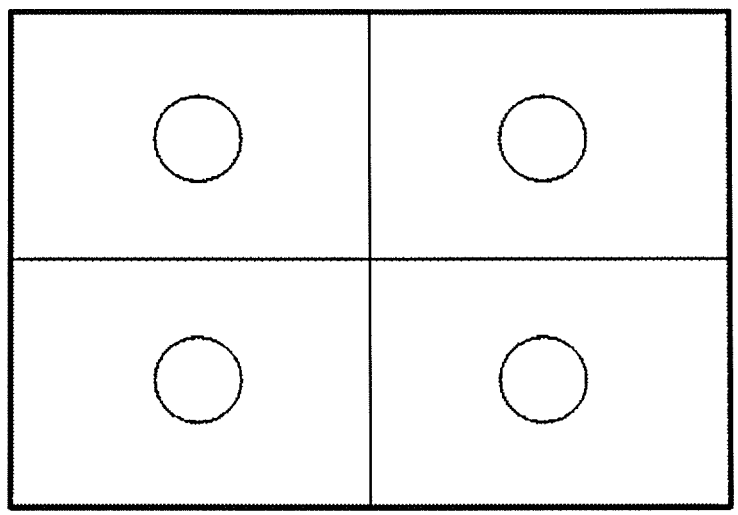
FIG. 20 is a view of an overlay pattern for use with the system for indicating an area of interest on an image as shown in FIG. 1, 1a, or 1b.
Figure 21:
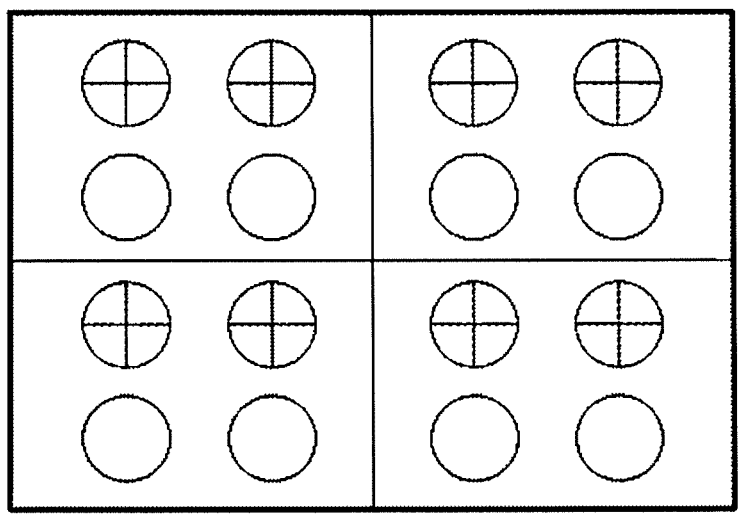
FIG. 21 is a view of an overlay pattern for use with the system for indicating an area of interest on an image as shown in FIG. 1, 1a, or 1b.

The overlay pattern may also include a key 36 for assisting the user in indicating and discussing areas or portions of the overlay pattern 30, and, in turn, indicating and discussing an area of interest on the underlying image data 34. In one example, the key 36 may include alphanumeric labels or coordinates. For example, as shown in FIG. 3 the rows and columns of a grid overlay may be labeled with letters and numbers—the vertical axis labeled with letters and the horizontal axis labeled with numbers (or vice versa) allowing reference to an area of the image with a simple letter-number combination (e.g. "C3" or "D2", etc.). In another embodiment, if the overlay pattern 30 comprises hash-marks as shown in FIG. 11, the hash marks may be labeled with coordinates. As shown in FIGS. 16 and 18, the quadrants or other defining shapes may be individually labeled with an alphanumeric key 36.

Certain properties of the overlay 30 and key 36 may be adjustable, including, but not limited to, the resolution (i.e., number of rows by number of columns, number of circles, etc.) of the overlay, the opacity of the overlay pattern 30 and/or key 36, the distribution of the opacity of the overlay pattern 30 and/or key 36, the color of the overlay 30 and/or key 36, the brightness of the overlay 30 and/or key 36, the thickness of the lines of the overlay pattern 30, the size of the font of the key 36, etc. The user may choose to enable the overlay pattern and set its properties prior to the start of the medical or surgical procedure, or the overlay may be enabled/disabled and the properties may be adjusted at any time during the medical or surgical procedure.

Figure 4:
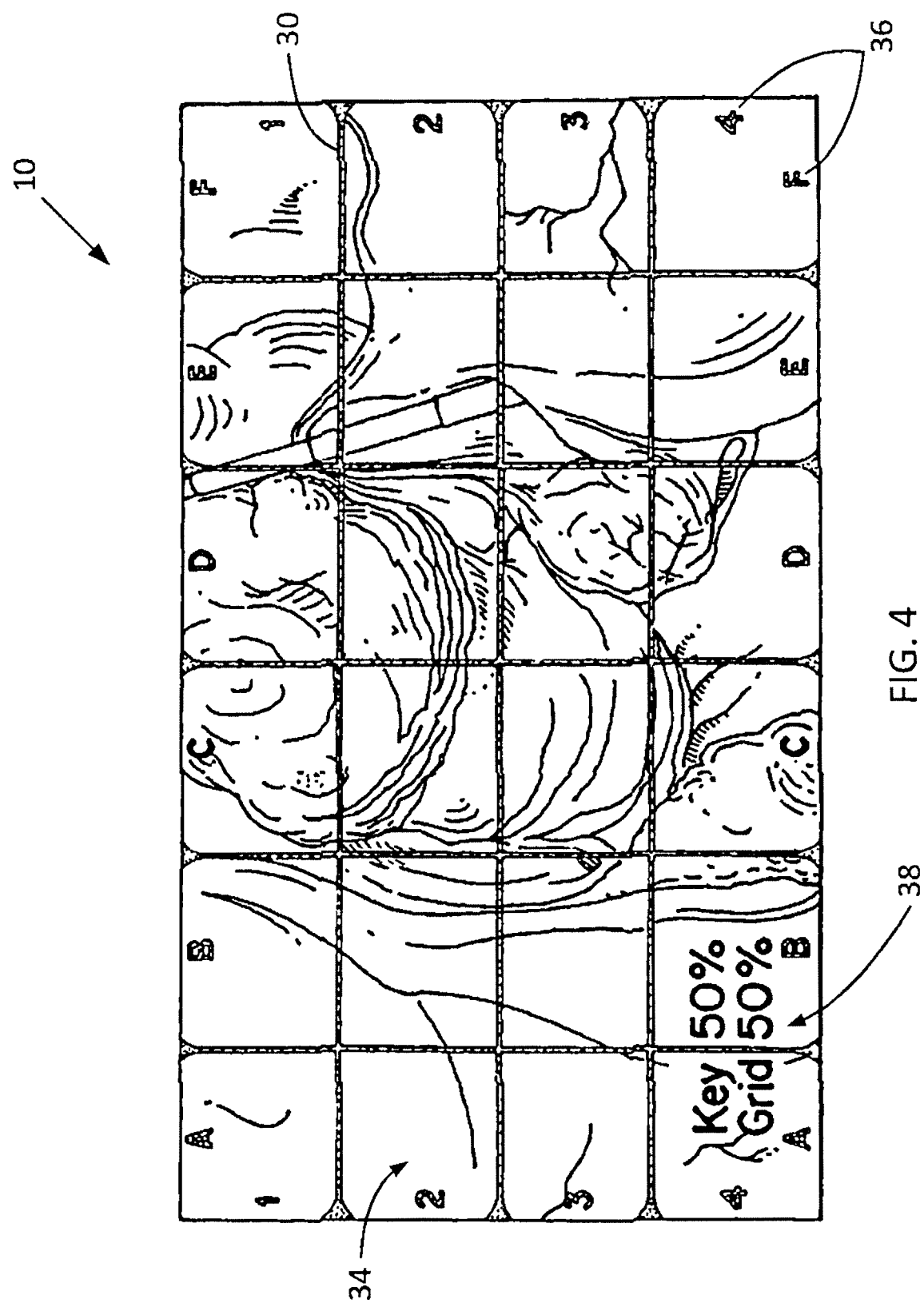
FIG. 4 is a view of an overlay pattern in the form of a grid with a key, both at 50% opacity, combined with image data, for use with the system for indicating an area of interest on an image as shown in FIG. 1, 1a, or 1b.

In one example, the overlay pattern 30 and key 36 can be applied to the image in varying levels of opacity. The overlay may also include an indicator 38, which may display certain properties of the overlay 30 as set by the user. For example, FIG. 3 illustrates the overlay 30 as a grid and key 36 applied at 100% opacity. FIG. 4 illustrates the overlay 30 and the key 36 both applied at 50% opacity. The properties of the overlay 30 can be constant or can vary across the display 32. For example, the overlay pattern 30 can be more opaque at the edges of the display 32 and gradually become more transparent toward the center of the display 32.

In a further embodiment, the adjustable properties of the overlay pattern and coordinates may be adjusted independently of one another. For example, as shown in FIG. 5, the overlay may be set to 50% opacity whereas the key 36 may be maintained at 100% opacity.

Various properties of the camera control unit (CCU) may also be changed so as to effect a change in the image data 34 at and/or around certain coordinates or a region of the overlay 30 identified by the user. For example, the brightness, contrast, color, or zoom of the image data 34 may be adjusted at and/or around the coordinates or region identified. The coordinates or region of the overlay 30 may be identified via an input 18, for example by button press on the source 12 or by touching an icon or the display window 26 of a touch screen 20. The system 10 may also be configured to include voice recognition of certain regions or coordinates of the overlay pattern 30 to change the properties of the CCU.

Moreover, the zoom level of the image data 34 may be adjusted independent of the overlay pattern 30. The resolution of the overlay pattern 30 will remain the same, while the image data 34 is zoomed in or out. For example, FIG. 6 illustrates a zoomed-in version of the image data 34 of FIG. 3, where the resolution of the grid overlay pattern remains constant (4 rows by 6 columns).

The user may set or adjust the properties of the overlay pattern 30 and/or the key 36 at the beginning of, or during, a surgical or medical procedure. For example, the user may select a grid overlay, choose the number of columns and rows, and set the color all at prior to commencing a surgical or medical procedure. The user may also establish presets to which the overlay 30 will default. In one embodiment shown in FIGS. 1-7, the resolution of the grid overlay is four rows by six columns. However, other grid overlay resolutions are contemplated, such as 4×4. The overlay can be of a varying number or a fixed number of columns, rows, quadrants, etc.

Figure 14:
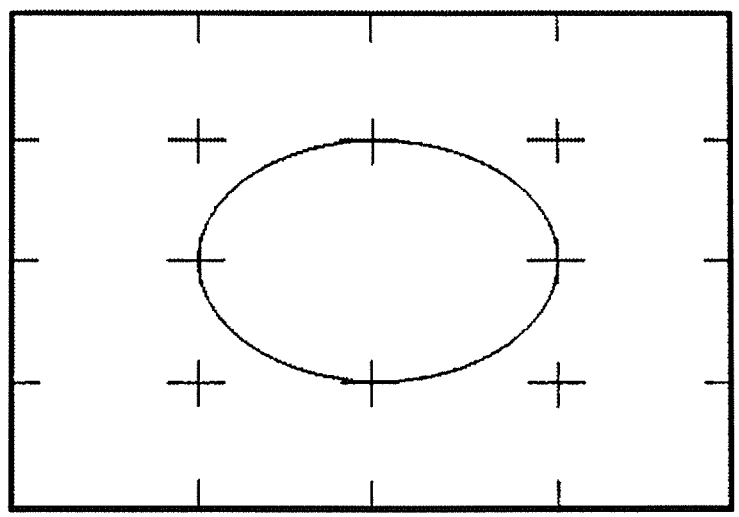
FIG. 14 is a view of an overlay pattern for use with the system for indicating an area of interest on an image as shown in FIG. 1, 1a, or 1b.
Figure 15:
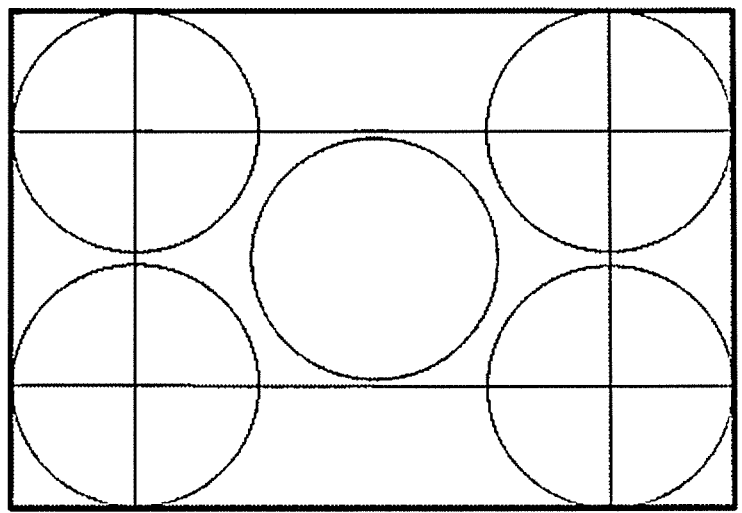
FIG. 15 is a view of an overlay pattern for use with the system for indicating an area of interest on an image as shown in FIG. 1, 1a, or 1b.

Additionally, the overlay pattern and/or resolution may be preset or chosen by the doctor in accordance with the aspect ratio of the display monitors. For example, the doctor may chose a standard definition (SD) display having a 4×3 aspect ratio and the overlay pattern would be chosen or adjusted accordingly. The doctor may also chose a high definition (HD) display having a 16×9 aspect ratio and the overlay pattern would be chose or adjusted accordingly. Overlay patterns incorporating ovals, such as the pattern shown in FIG. 15, are well suited for HD displays whereas overlay patterns incorporating circles, such as the pattern shown in FIG. 14, are well suited for SD displays.

In a further embodiment, the system 10 may automatically enable the overlay if a motion vector detector senses a still image for a certain period of time. Conversely, the system 10 may automatically disable the overlay if a motion vector detector senses a moving image for a certain period of time. Further, the system 10 may automatically "time out" after the overlay has been enabled for a preset period of time, or "time-out" if the image has been still for a certain period of time.

When the overlay is enabled or disabled, either by automatic sensing, "time-out", or by direct input from the user, the overlay could be programmed to either immediately appear at 100% opacity or immediately disappear. Alternatively, the overlay could be programmed to gradually appear or disappear by gradual increase or decrease in opacity. These properties will be discussed further below.

Figure 22:
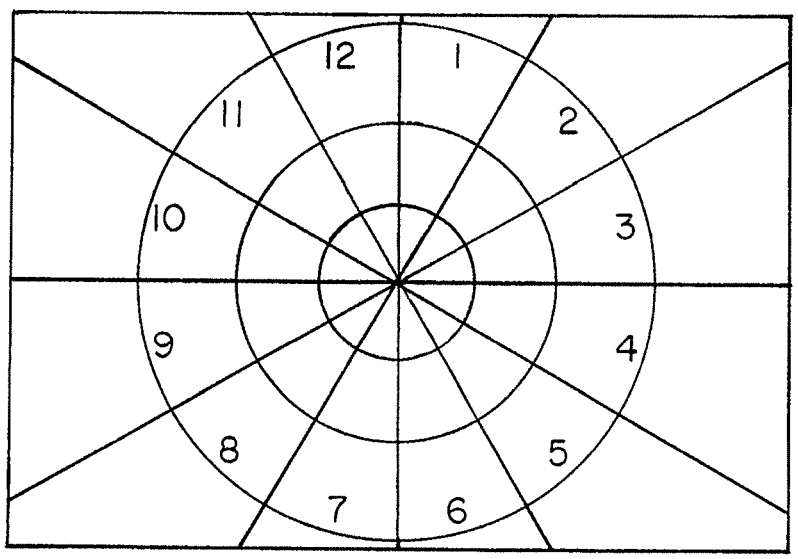
FIG. 22 is a view of an overlay pattern for use with the system for indicating an area of interest on an image as shown in FIG. 1, 1a, or 1b.
Figure 24:
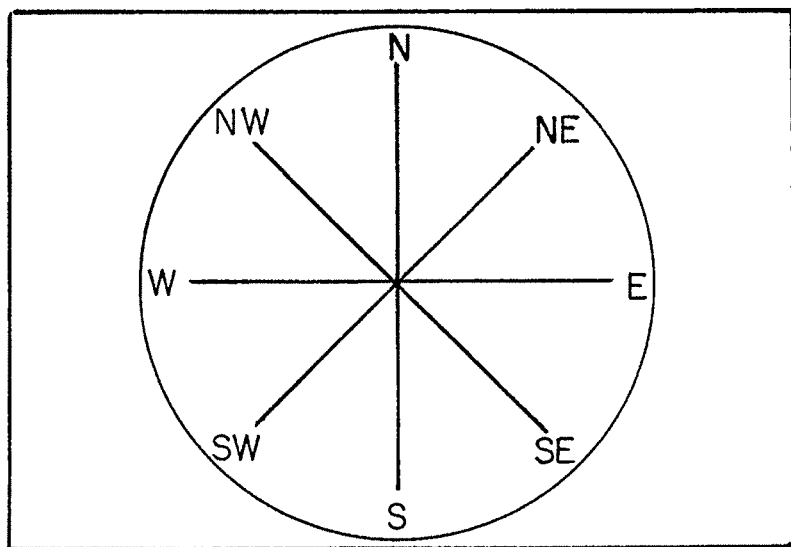
FIG. 24 is a view of an overlay pattern for use with the system for indicating an area of interest on an image as shown in FIG. 1, 1a, or 1b.
Figure 25:
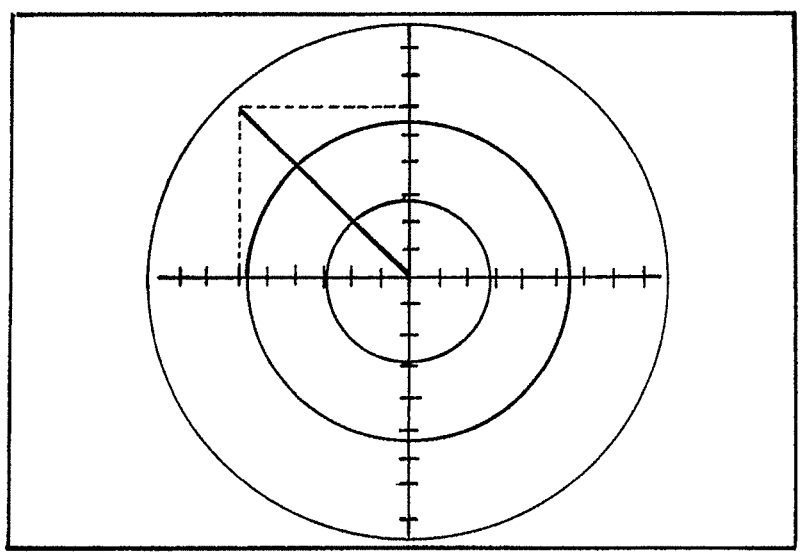
FIG. 25 is a view of an overlay pattern for use with the system for indicating an area of interest on an image as shown in FIG. 1, 1a, or 1b.

In addition to the overlay pattern recited before, the overlay pattern may include a set of centric lines originating from a single point, such as from the center of the monitor screen, and optionally ending near the edges of the monitor screen, as shown in FIGS. 22, 24 and 25. Preferably, the centric lines are shown for every 15 degrees, 20 degrees, 30 degrees, 45 degrees, 60 degrees, 90 degrees, or other predetermined degrees. When the centric lines are shown for every 30 degrees, the circular overlay pattern is "clock" like. When the centric lines are shown for every 45 degrees, the circular overlay pattern is "compass" like. When the centric lines are shown for every 90 degrees, the circular overlay pattern is a "quadrant" like.

Figure 23:
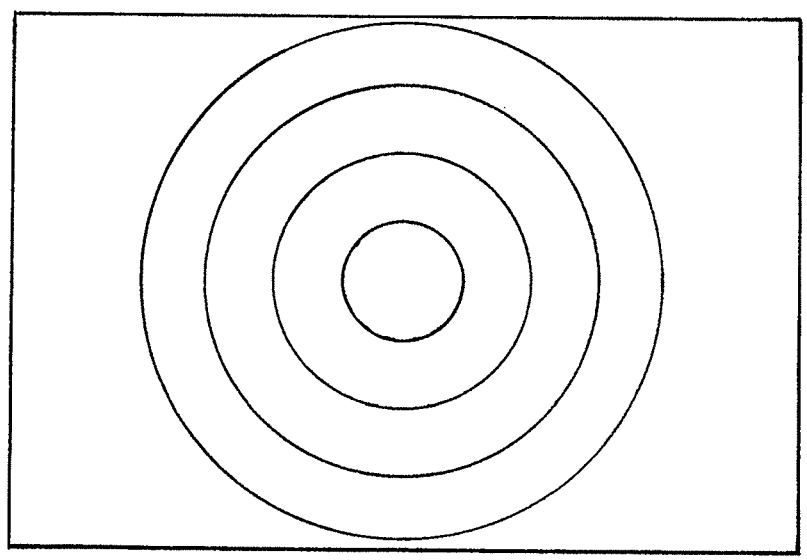
FIG. 23 is a view of an overlay pattern for use with the system for indicating an area of interest on an image as shown in FIG. 1, 1a, or 1b.

The overlay pattern may include a series of concentric shapes. Preferably, the concentric shapes are concentric circles, concentric ovals, or concentric polygons. More preferably, the concentric shapes are concentric circles (also called centric circles), as shown in FIGS. 22, 23 and 25. In one embodiment, as shown in FIGS. 22 and 25, the overlay pattern contains three concentric circles, at 25%, 50% and 100% of the monitor height.

The overlay pattern may be formed by superimposing the centric lines on the concentric shapes, as shown in FIGS. 22, 24 and 25. In one embodiment, the overlay pattern is formed by a wind rose going from 0 degree to 360 degrees with centric lines at every 20 degree or 30 degrees and two concentric circles at 25% and 50% of the monitor height. Preferably, the single originating point of the centric lines is also the center of the concentric shapes.

As stated before, the overlay pattern may include an optional key 36 for assisting the user in indicating and discussing areas or portions of the overlay pattern 30, and, in turn, indicating and discussing an area of interest on the underlying image data 34.

For the "clock" like overlay pattern as shown in FIG. 22, the centric lines may be labeled as 1, 2, 3, . . . , 12, corresponding to the conventional positions of 1 o'clock, 2 o'clock, 3 o'clock, . . . 12 o'clock. For the "compass" like overlay pattern, as shown in FIG. 24, the centric lines can be marked as N, NE, E, SE, S, SW, W, and NW, corresponding to a conventional compass. The "quadrant" like overlay pattern, as shown in FIG. 25, may be labeled as x-axis and y-axis, which may in turn be labeled with numbers as conventional coordinates.

The concentric circles can be labeled with an alphanumeric key, or other suitable number and/or letter characters. If there are a total of three concentric circles, they can be referred as inner, medium, and outer circles, or small, middle, and large circles.

The overlay patterns formed by superimposing the centric lines on the concentric circles are particular useful for indicating areas of interest in some circumstances. For instance, the small circle of FIG. 22 is suitable for showing a small circular image, such as an image of 4 mm scope or a magnified laparoscopic image. Thus the small circle of FIG. 22 can be used for indicating the precise targeting area of an image object, leaving the other area of the imaged object outside the small circle. To further highlight the image area within the small circle, the small circle of the concentric circles can be made transparent, while the area outside the small circle gradually becomes opaque.

The designs of concentric shapes, centric lines, concentric shapes superimposed on centric lines, and the previously described designs, such as grid, crosshair, quadrant, hash mark, can be used interchangeably for the overlay pattern 30. Collectively, they form a plurality of designs for the overlay pattern 30.

Figure 1A:
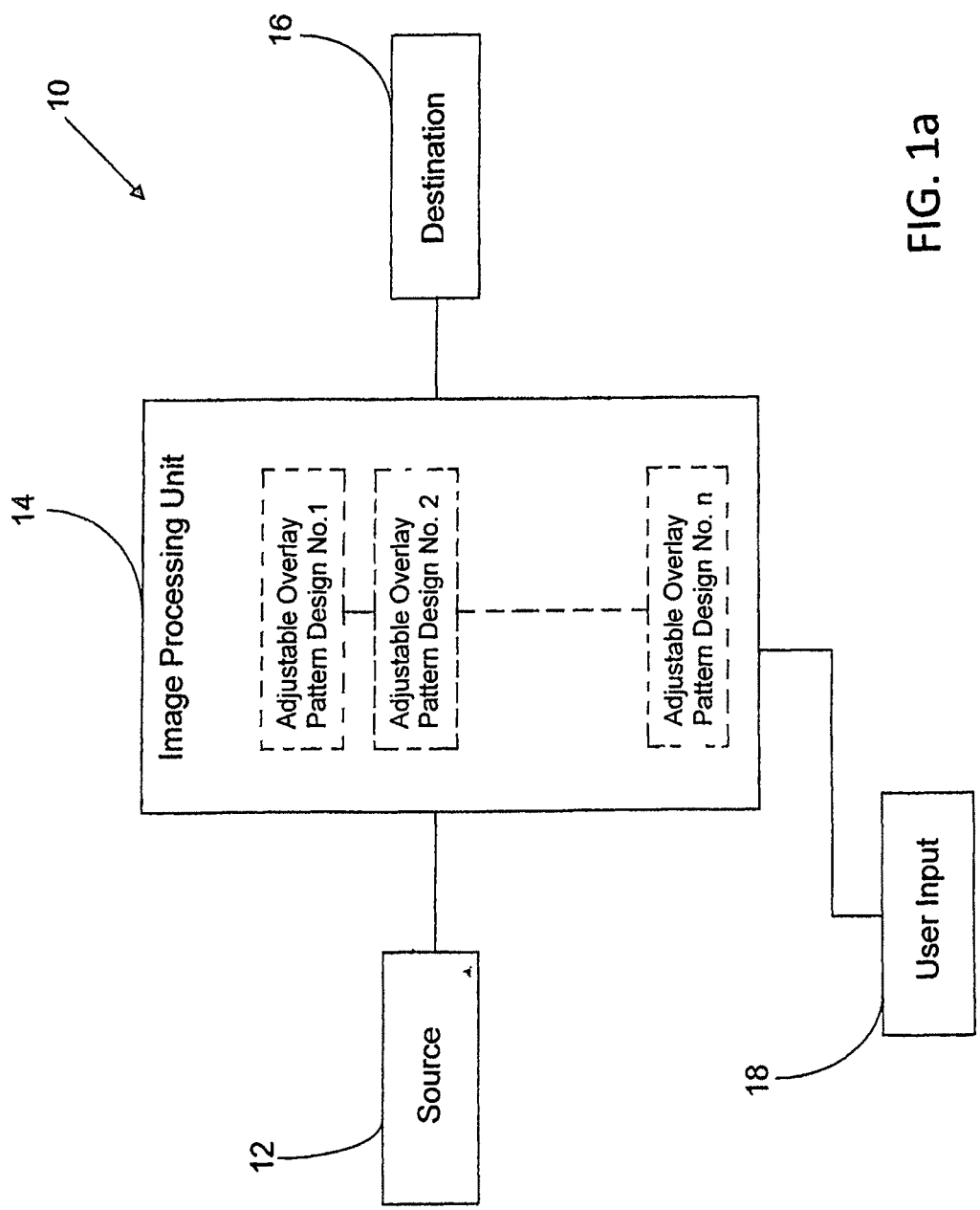
FIG. 1a is a schematic illustration of one embodiment of a system for indicating an area of interest on an image, which includes a plurality of designs for an overlay pattern available in an image process unit.

As illustrated in FIG. 1a, the system 10 in accordance with the present invention may include a source 12, an image processing unit 14, and a destination 16. The source 12 is typically connected with the processing unit 14 by wires or cables to transmit image data 34. However, the source 12 may also wirelessly transmit signals to the processing unit 14. The process unit 14 includes a plurality of designs for the overlay pattern 30 to suit different display needs, and software executing on the image processing unit for combining the image data 34 from the source 12 with an overlay pattern 30 and further adjusting the properties of the overlay pattern, such as activation, deactivation, resolution, opacity, opacity distribution, color, brightness, thickness, and size. The software can also be configured to select the desired overlay pattern 30 in response to a user input 18. The user input 18 can be provided by a manual command, a voice command, or preset by a user prior to a surgical or medical procedure. For enabling the user input 18 via a voice command, the software is configured with voice recognition features. The plurality of the overlay pattern designs can be numbered for easy identification and selection.

As described above, the zoom level of the image data 34 may be adjusted independent of the overlay pattern 30, and the software executing on the image processing unit may be configured to enable this feature. Unlike the prior art references that use the overlay as part of a reference for measurement, which usually require the overlay pattern 30 and the image data 34 be zoomed in or out at the same level simultaneously, the present invention uses the overlay pattern as an aid to allow a doctor or other observers to identify an area of interest, which often requires keeping the overlay pattern 30 constant while zooming in or out of the areas of interest. Since size measurement of an imaged object is not required, the apparatus of the present invention does not include other components usually associated with the size measurement. As a result, the apparatus of the present invention is simple and cost effectiveness for its intended purpose.

By selecting and superimposing the overlay pattern 30 with optional key 36 on an image, the present invention eliminates the need of using a laser pointer, cursor, "circling," or other annotating or marking means by a person to identify areas of interest, as required by the prior art. Thus the present invention provides an effective and clear communication regarding certain areas of interest displayed on the live monitor.

Figure 1B:
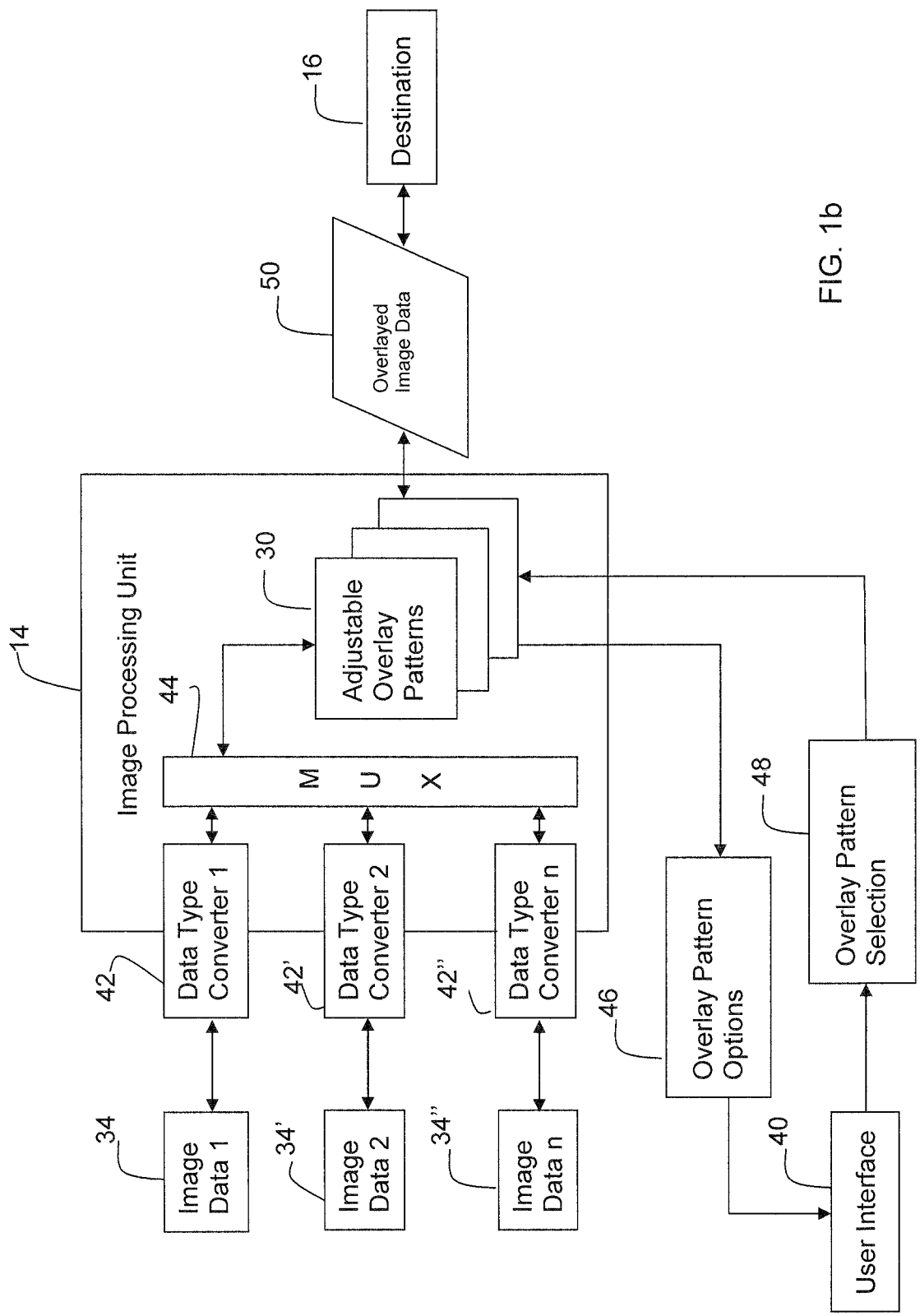
FIG. 1b is a schematic illustration of one embodiment of a system for indicating an area of interest on an image, which includes multiple image data sources for display.

As illustrated in FIG. 1b, the system 10 may comprise multiple sources of image data 34, 34', 34". The types of image data may include, but are not limited to, ultrasound, X-ray, magnetic resonance imaging, nuclear magnetic resonance imaging, magnetic resonance tomography, computed tomography, and surgical image data. The image data 34, 34', 34" may be in the form of video data, still frame data or combinations thereof. The image data 34, 34', 34" may be retrieved from a non-imaging source, such as an image archive, PC, or other source of image data. The image data 34, 34', 34" may also be streamed from a medical instrument that generates the image data 34, 34', 34".

To accommodate different types of image data 34, 34', 34", data type converters 42, 42', 42" may be utilized to convert the image data 34, 34', 34" into a format that is readable by the image processing unit 14 before the image data 34, 34', 34" is transmitted to the image processing unit 14. The formatted data may be saved in a storage device. The system 10 may include one data type converter for all the data conversions, or multiple data type converters for multiple sources of image data. In some embodiments, each source of image data is provided with one data type converter, which is specifically adapted to convert the particular type of image data. Each of the data type converters 42, 42', 42" may be a standalone unit. Alternatively, it may be part of the medical device or camera that generates the image data 34, 34', 34" or part of the image processing unit 14. In some embodiments, the communications among the image data 34, 34', 34", the data type converters 42, 42', 42", and the image processing unit 14 are bi-directional. The communications are typically performed via wires or cables. However, the image data 34, 34', 34" and the formatted image data may also be wirelessly transmitted.

An input multiplexer/combiner 44 may be used to facilitate input to the processing unit 14 from multiple imaging sources. In principle, any practical number of input sources of any configuration or having any capabilities may be input in this way. Alternatively, the processing unit 14 may accept input from only one image source or otherwise omit the multiplexer 44 without departing from the invention. In some embodiments, the multiplexer 44 may include a data type converter 42, 42', 42" for converting or formatting the data type of incoming image data, thereby eliminating the need to have other data type convertors in the system. The multiplexer 44 may be part of the image processing unit 14 as shown in FIG. 1b. Alternatively, it can be a standalone unit outside the image processing unit 14.

The process unit 14 includes a plurality of adjustable overlay patterns 30 to suit different display needs, and software (not shown) executing on the image processing unit for selecting the desired overlay pattern(s) in response to a user input and for combining the image data selected through the multiplexer/combiner 44 with the desired overlay pattern(s) to generate overlayed image data 50.

For enabling the user input, overlay pattern options 46 may be transmitted to a user interface 40 for a user to select at least one overlay pattern from the plurality of adjustable overlay patterns 30. The user may provide input by a manual command, a voice command, or preset by a user prior to a surgical or medical procedure. For enabling user input via a voice command, the software may be configured with voice recognition features. The plurality of the overlay pattern designs may be numbered for easy identification and selection. After that, the data containing the overlay pattern selection 48 by the user may be transmitted to the processing unit 14. The communications between the processing unit 14 and the user interface 40 may be conducted through wires/cables or wireless.

During the combining process of the image data and the overlay pattern, the image may be oriented so that an area of interest on the image is located near or at an identifiable region of the overlay pattern. In this way, a user may identify the area of interest on the image without having to use a laser pointer or cursor, or otherwise "circle" or annotate on the image. It would be apparent to those skilled in the art as to an identifiable region of each overlay pattern. For instance, for an overlay pattern of concentric circles, the identifiable region may be the smallest circle; for an overlay patter of quadrants, the identifiable region may be the upper left quadrant; and for an overlay pattern of crosshairs, the identifiable region may be one of the crosshairs. Because the overlay patterns have distinctive shapes, alphanumeric labels and coordinates, the regions of the overlay patterns may be verbally identified by making reference to the shapes, alphanumeric labels, coordinates, etc. The software may also be configured to be able to adjust the properties of the overlay pattern and of the images independently. For instance, the image may be zoomed in while the overlay pattern is kept constant in order to create an enlarged, detailed view of the area of interest on the image.

The overlayed image data 50 may be transmitted to destination 16, which typically includes a display. The display may have picture-in-picture (PIP) capabilities which allow display of two images. For instance, the PIP display may simultaneously show an ultrasound image and a magnetic resonance image, either with or without an overlay pattern. Alternatively, the PIP display may simultaneously show one overlayed image and one image without an overlay, each of the images may have different zoom levels. The destination 16 may also include a storage device for saving the overlayed image data 50.

It should be understood that the foregoing is illustrative and not limiting, and that obvious modifications may be made by those skilled in the art without departing from the spirit of the invention.

What is claimed is:

1. A medical imaging system for indicating an area of interest on an image, comprising:
   multiple sources of image data including an endoscopic camera acquiring images;
   a camera control unit having an image processing unit in communication with said multiple sources of image data through data type converters, said data type converters adapted to convert each of said multiple sources of image data received by the camera control unit into formatted image data readable by said image processing unit;
   a plurality of overlay patterns stored on the camera control unit;
   a user interface receiving user input for selecting an overlay pattern from said plurality of overlay patterns;
   software executing on said image processing unit for combining said selected overlay pattern with said formatted image data to indicate an area of interest; and
   a plurality of destinations for receiving said combined selected overlay pattern and formatted image data, including a first display in a sterile area and a second display outside of the sterile area;
   wherein the software is configured to change a zoom level of said formatted image data when combined with said selected overlay pattern, such that properties of selected overlay pattern remain constant and are not affected by changing the zoom level of the formatted image data.

2. The system of claim 1 wherein said multiple sources of image data are selected from a group consisting of ultrasound, X-ray, magnetic resonance imaging, nuclear magnetic resonance imaging, magnetic resonance tomography, computed tomography, and surgical image data.

3. The system of claim 1 wherein at least one of the multiple sources of image data communicates with said image processing unit via live streaming, and at least another one of the multiple sources of image data is from storage.

4. The system of claim 1 wherein said system comprises a multiplexer in the camera control unit, wherein said image processing unit communicates with said multiple sources of image data through said multiplexer.

5. The system of claim 4 wherein the data type converters each convert one of the multiple sources of image data from a different type of image data into formatted image data readable by said image processing unit.

6. The system of claim 1 wherein said software is further configured to adjust said formatted image data until said area of interest on said formatted image data is located at or near a region of said selected overlay pattern.

7. The system of claim 1 wherein said selected overlay pattern includes a key for indicating one or more regions of said overlay pattern.

8. The system of claim 1 wherein said plurality of overlay patterns include a grid, crosshairs, quadrants, marks, a circle, an oval, concentric shapes, centric lines, and a combination thereof.

9. The system of claim 8 wherein said concentric shapes are two concentric circles having the diameters at 25% and 50% of the height of said first display.

10. The system of claim 8 wherein said centric lines are shown for every 15 degrees, 20 degrees, 30 degrees, 45 degrees, 60 degrees, or 90 degrees.

11. The system of claim 8 wherein said overlay pattern comprises concentric circles superimposed on a set of centric lines originated from a single point, said single point being the center of said concentric circles.

12. The system of claim 1 wherein said software is configured to configure at least one property of said properties of said selected overlay pattern.

13. The system of claim 12 wherein said at least one property of said selected overlay pattern is chosen from the group consisting of activation, deactivation, resolution, opacity, opacity distribution, color, brightness, thickness, and size.

14. The system of claim 12 wherein the at least one property of said selected overlay pattern is configured in response to a command by a user.

15. The system of claim 12 wherein the at least one property of said selected overlay pattern is configured in response to a passage of time.

16. The system of claim 12 wherein the at least one property of said selected overlay pattern is configured in response to data input from a motion vector detector or an accelerometer.

17. The system of claim 1 wherein said first display is configured to present said formatted image data or said combined selected overlay pattern and formatted image data as a picture-in-picture.

18. The system of claim 1 further comprising a storage device for saving said combined selected overlay pattern and formatted image data.

19. The system of claim 1 wherein the user interface comprises a button on the endoscopic camera.

20. The system of claim 19 wherein actuation of the button enables or disables the selected overlay pattern.

21. The system of claim 1 wherein one of the multiple sources of image data comprises video image data, and another one of the multiple sources of image data comprises ultrasound image data, both of which of are converted into the formatted image data for combining with said selected overlay pattern.

22. The system of claim 1 wherein the formatted image data comprises image data from more than one of said multiple sources of image data.

23. The system of claim 1 wherein there is a preset overlay pattern for the first display.

24. A method for identifying an area of interest on an image comprising the steps of:
   providing multiple sources of image data, including images acquired with an endoscopic camera;
   transmitting image data of said multiple sources of image data to an image processing unit on a camera control unit;
   providing a plurality of overlay patterns;
   selecting an overlay pattern from said plurality of overlay patterns based on user input;

combining said image data with said selected overlay pattern in said image processing unit to indicate an area of interest;
transmitting said combined image data and selected overlay pattern to a first display in a sterile area and a second display outside of the sterile area; and
displaying said combined image data and selected overlay pattern on said first and second displays;
changing a zoom level of said image data when combined with said selected overlay pattern, such that properties of selected overlay pattern remain constant and are not affected by changing the zoom level of the image data, wherein said multiple sources of image data are selected from a group consisting of ultrasound, X-ray, magnetic resonance imaging, nuclear magnetic resonance imaging, magnetic resonance tomography, and computed tomography.

\* \* \* \* \*